United States Patent [19]
Lord et al.

[11] Patent Number: 5,257,971
[45] Date of Patent: Nov. 2, 1993

[54] RECONDITION PROCESS FOR A MEDICATION INFUSION PUMP

[75] Inventors: Peter C. Lord, Valencia; William P. VanAntwerp, Westchester, both of Calif.

[73] Assignee: MiniMed Technologies, Ltd., Sylmar, Calif.

[21] Appl. No.: 32,037

[22] Filed: Mar. 16, 1993

[51] Int. Cl.$^5$ ............................................. A61M 31/00
[52] U.S. Cl. ................................. 604/49; 604/153
[58] Field of Search ........................ 604/28, 49, 153

[56] References Cited

U.S. PATENT DOCUMENTS

| | | | |
|---|---|---|---|
| 4,112,947 | 9/1978 | Nehring | 604/28 |
| 4,688,231 | 5/1981 | de Vries et al. | 604/153 |
| 4,710,177 | 12/1987 | Smith et al. | 604/153 |
| 4,767,399 | 8/1988 | Bollish | 604/28 |
| 4,898,585 | 2/1990 | Borsany et al. | 604/153 |
| 5,053,031 | 10/1992 | Borsanyi | 604/153 |

Primary Examiner—Paul J. Hirsch
Attorney, Agent, or Firm—Leslie S. Miller; Stuart O. Lowry

[57] ABSTRACT

A method is provided for reconditioning a medication infusion pump by removal of accumulated medication deposits and the like to restore pump performance without requiring surgical removal of an implanted pump from a patient. The reconditioning process comprises sequential delivery of a buffer solution and a rinse solution to internal pump flow passages. The rinse solution is effective to dissolve medication deposits and the like within narrow pump flow passages before the rinse solution is neutralized by intermixing with the buffer solution. Dissolution of accumulated medication deposits results in restoration of pump performance substantially to original product specifications.

23 Claims, 2 Drawing Sheets

RECONDITION PROCESS FOR A MEDICATION INFUSION PUMP

BACKGROUND OF THE INVENTION

Field of the Invention

The present invention relates generally to me infusion pumps, particularly of the type adapted for implantation directed into the body of a patient and for programmed operation to deliver medication to the patient, and more particularly to a reconditioning process for effectively removing accumulated medication-based deposits and the like from internal flow pump passages to restore pump performance characteristics, without requiring an implanted pump to be surgically removed from a patient.

Medication infusion pumps are generally known in the art for use in delivering a selected medication to a patient in a scheduled or preprogrammed manner. In recent years, infusion pumps have been developed in compact form and adapted for direct implantation into the body of a patient, to deliver a specific medication such as insulin to the patient in discrete doses over an extended time period. An implantable infusion pump of this general type includes an internal medication chamber or reservoir for receiving and storing a supply of the selected medication in liquid form, in combination with a miniature pump mechanism and associated programmable control means for operating the pump mechanism to deliver discrete doses of the medication from the internal storage reservoir and through a catheter to the patient. For one illustrative example of an implantable medication infusion pump of this general type, see U.S. Pat. No. 4,573,994, to Fischell et al.

The internal pump mechanism typically comprises an electromagnetically driven pulsatile pump having a solenoid operated piston mounted for reciprocation within a cylinder to draw medication from the storage reservoir, and to deliver the medication through the catheter to the patient. The pulsatile piston operates in conjunction with an inlet check valve having a spring-loaded valve member movable between open and closed positions with respect to an inlet valve seat. The valve member and the valve seat are normally constructed from biocompatible and relatively inert materials, such as a movable valve disk of a silicone elastomer and a rigid annular valve seat defined at the end of a ferrule formed of a titanium or titanium alloy. For examples of pulsatile pump mechanisms used in implantable infusion pumps, see U.S Pat. No. 4,568,250, to Falk et al.; U.S. Pat. No. 4,569,641, to Falk et al.; U.S. Pat. No. 4,636,150, to Falk et al.; and U.S. Pat. No. 4,714,234, to Falk et al.

Despite the relatively inert characteristics of the traditional valve member and valve seat materials, medication deposits having a particle-like structure are known to accumulate over a period of time, especially in the vicinity of the valve seat. The formation of such medication deposits is believed to be attributable to shear denaturation and/or precipitation of pharmaceutical components in response to relatively high mechanical stresses applied to the medication in the immediate vicinity of the valve seat, as the valve member moves between the open and closed positions. Such deposits are especially likely when relatively complex medications having a relatively large molecular structure are used, such as protein-based pharmaceuticals including insulin and others.

Moreover, protein and other organic constituents present in such pharmaceuticals exhibit a tendency to adhere to the surface of titanium metal components, resulting in an accumulation of proteinaceous deposits within internal pump flow passages. Such medication deposits can obstruct narrow flow passages within the pump, resulting in a deterioration in pump performance. Moreover, accumulated deposits at the inlet check valve can over time result in valve leakage, typically in the form of undesirable backflow of body fluids into the medication reservoir. In the past, when these problems have arisen, it has been necessary to use a surgical procedure to remove and replace the infusion pump.

There exists, therefore, a need for a process or procedure for reconditioning an implanted medication infusion pump by safely cleaning and removing the accumulated medication deposits from internal pump flow passages, without requiring surgical removal of the implanted pump from a patient. It is accordingly the objective of the present invention to fulfill these needs and to provide further related advantages.

SUMMARY OF THE INVENTION

The disadvantages and limitations of the background art discussed above are overcome by the present invention. With this invention, a reconditioning process is provided for in situ removal of medication-based deposits and the like from the internal flow passages of a medication infusion pump, for purposes of restoring pump operating performance substantially to original product specifications without requiring surgical removal of an implanted pump from a patient. In general terms, the process comprises sequential delivery of a buffer solution and a rinse solution with either a high pH (alkaline) or a low pH (acid) to internal pump flow passages of the medication infusion pump. A preferred solution is sodium hydroxide, which is an alkaline. The rinse solution is effective to dissolve accumulated deposits before neutralization upon intermixture with the buffer solution.

The medication infusion pump comprises a compact housing which in the preferred form is adapted for implantation directly into the body of a patient. A medication reservoir within the pump housing contains a supply of a selected medication, such as insulin for administration to a diabetic patient in controlled doses, in response to programmed operation of an internal pump mechanism. A refill port on the pump housing permits transcutaneous refilling of the medication reservoir. Accumulation of medicationbased deposits within the internal flow passages of the pump mechanism, particularly at an inlet check valve can cause deterioration in pumping characteristics and may eventually prevent proper seating of the inlet check valve, resulting in undesired back-flow leakage of body fluids into the medication reservoir.

The reconditioning process of the present invention includes the step of filling the medication reservoir with a selected buffer solution, and then operating the pump mechanism to substantially fill the internal flow passages thereof with the buffer solution. The buffer solution may be any buffer solution which is capable of neutralizing the rinse solution. For example, in an insulin pump insulin diluent could be used. If an alkaline rinse solution such as sodium hydroxide is to be used, the buffer solution may be, for example, potassium phosphate.

The medication reservoir may then be aspirated to remove the buffer solution therefrom, after which the reservoir is filled with the selected rinse solution, such as the alkaline rinse solution of sodium hydroxide. The pump mechanism is operated to deliver a selected volumetric dose of the rinse solution into the internal flow passages thereof.

The rinse solution effectively dissolves medication deposits, especially in the vicinity of the inlet check valve, before neutralization upon contact and intermixture with the buffer solution. Dissolution of those medication deposits effectively opens narrow pump passages previously obstructed by the deposits, and further permits the check valve to close and seal in a normal manner, thereby restoring pump performance substantially to original product specifications. Residual buffer and rinse solution is aspirated from the medication reservoir, after which the medication reservoir is filled with the selected medication and normal pump operation is resumed. Throughout the operation, only neutralized material actually reaches the patient.

Other features and advantages of the invention will become more apparent from the following detailed description taken in conjunction with the accompanying drawings, which together illustrate, by way of example, the principles of the invention.

DESCRIPTION OF THE DRAWINGS

These and other advantages of the present invention are best understood with reference to the drawings, in which.

DETAILED DESCRIPTION OF THE PREFERRED EMBODIMENT

Figure 1:
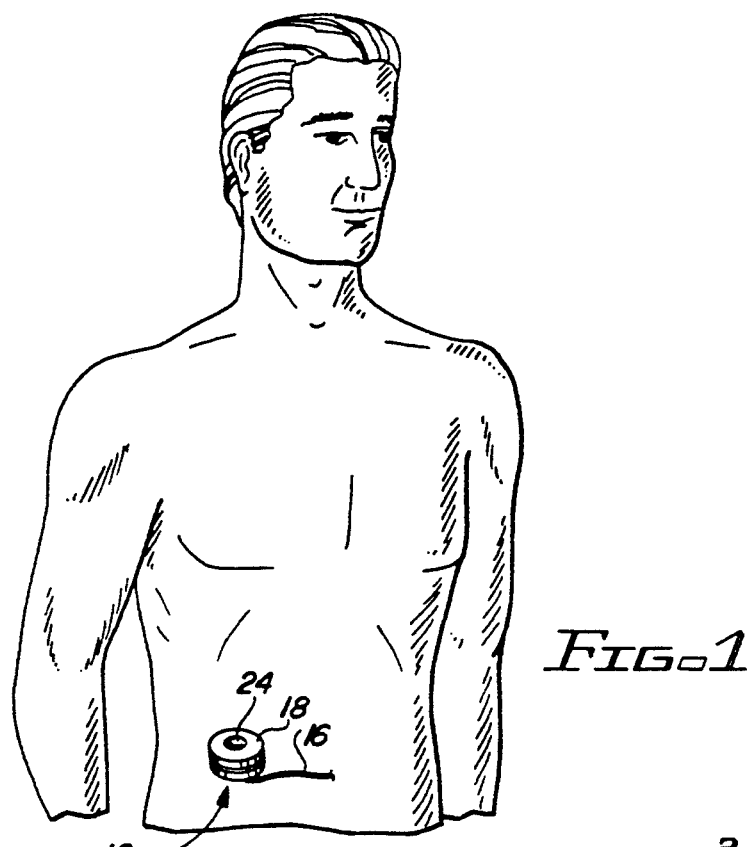
FIG. 1 is a perspective and somewhat schematic view representing a typical implantable medication infusion pump.
Figure 2:
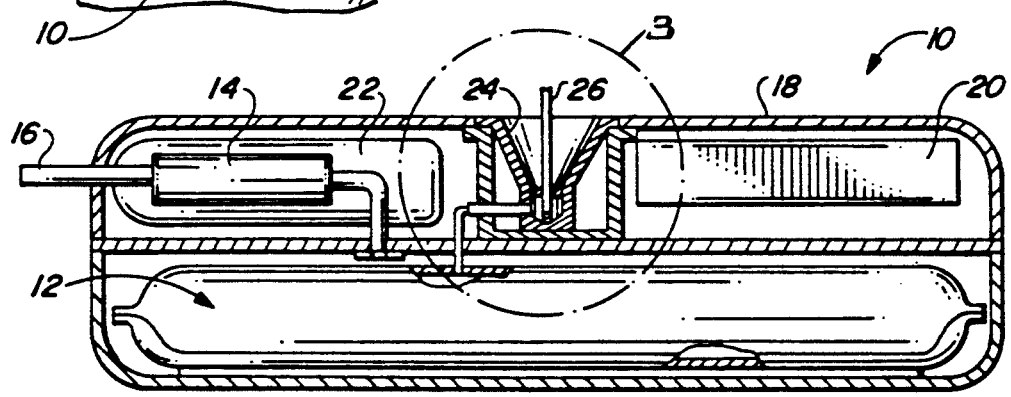
FIG. 2 is an enlarged and somewhat schematic vertical sectional view of the pump illustrated in FIG. 1, showing an internal pump mechanism for delivering medication from an internal storage reservoir to a patient.

As shown in the exemplary drawings, an implantable medication infusion pump referred to generally in FIGS. 1 and 2 by the reference numeral 10 is provided for use in administering a selected medication to a patient in a controlled, preprogrammed manner. The infusion pump 10 receives and stores a quantity of the selected medication within an internal medication chamber or reservoir 12 (FIG. 2). The internal medication chamber 12 may be of the type shown in FIG. 2, or it may also be a flexible metal bellows reservoir as shown in U.S. Pat. No. 4,573,994, to Fischell et al.

A miniature pump mechanism 14 is provided for delivering the medication from the chamber 12 through a catheter 16 to the patient. In accordance with the invention, a reconditioning process is provided for in situ cleaning and removal of accumulated medication deposits within narrow flow passages of the pump mechanism 14, without requiring surgical removal of the pump 10 from the patient.

As is known in the art, the illustrative medication infusion pump 10 comprises a small substantially self-contained unit adapted for direct implantation into the body of a patient. The pump 10 comprises an hermetically sealed pump housing or case 18 formed from a biocompatible material, such as titanium or titanium alloy. The pump housing 18 defines the internal medication chamber 12 for receiving and storing the supply of the selected medication in liquid form, such as insulin for a diabetic patient. The pump housing 18 encases the internal pump mechanism 14 in combination with electronic control circuitry 20 and battery 22 for periodically operating the pump to deliver medication doses via the catheter 16 to the patient.

Figure 3:
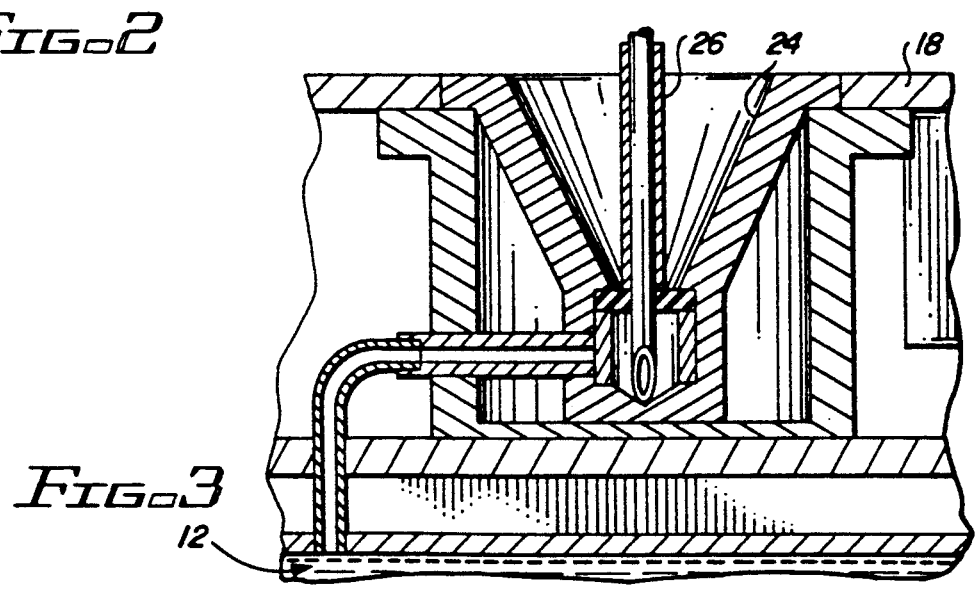
FIG. 3 is a further enlarged and somewhat schematic sectional view corresponding with the encircled region 3 illustrated in FIG. 2, showing a refill port on the implantable pump.

The control circuitry 20 is suitably preprogrammed to deliver the medication in accordance with individual patient need. An inlet or refill port fitting 24 on the pump housing 18 is adapted to receive a hypodermic needle 26 (FIG. 3) to permit percutaneous refilling of the medication chamber 12 without requiring surgical access to the infusion pump 10. For a more detailed description of the overall construction and operation of implantable infusion pumps of this general type, see U.S. Pat. No. 4,373,527, to Fischell; and U.S. Pat. No. 4,573,994, to Fischell et al., both of which are hereby incorporated herein by reference.

Figure 4:
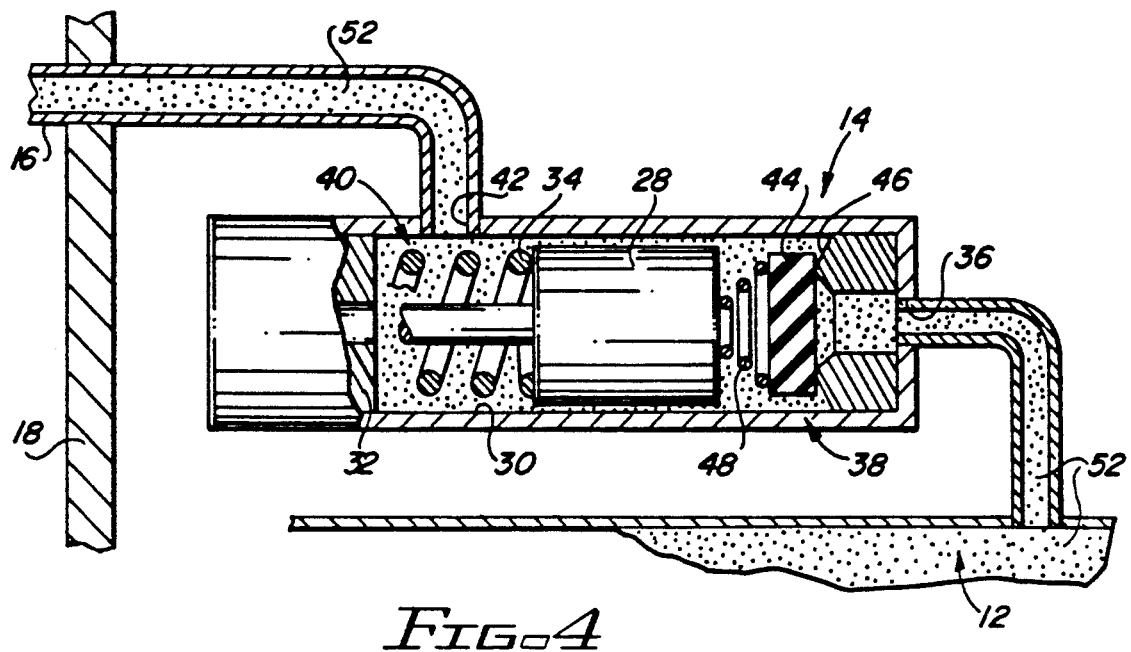
FIG. 4 is an enlarged and somewhat schematic sectional view illustrating portions of an internal pump mechanism, showing the step of filling of internal pump flow passages with a buffer solution.

As shown generally in FIG. 4, the internal pump mechanism 14 comprises a positive displacement, solenoid operated pulsatile pump device having a piston 28 adapted for reciprocal displacement within a pump cylinder 30. In this regard, the piston 28 is drawn electromagnetically by a coil 32 in a first direction, followed by a return stroke in an opposite, second direction under the influence of a return spring 34. With this reciprocal action, the piston 28 functions to draw the medication into the pump cylinder 30 via an inflow port 36, past an inlet check valve 38 into the pump cylinder, followed by delivery of the medication through an outflow chamber 40 and associated outflow port 42 to the catheter 16.

The check valve 38 comprises a valve member 44 movably carried at one end of the piston 28 for engaging an annular valve seat 46 which circumscribes the inflow port 36. A biasing spring 48 is interposed between the piston 28 and the valve disk 44 for spring-loading the valve disk toward a closed position seated upon the valve seat 46, as the piston 28 strokes toward the valve seat. Further details of the overall construction and operation of the pump Mechanism 14 may be found by reference to U.S. Pat. No. 4,568,250, to Falk et al.; U.S. Pat. No. 4,569,241, to Falk et al.; U.S. Pat. No. 4,636,150, to Falk et al.; and U.S. Pat. No. 4,714,234, to Falk et al., all of which are hereby incorporated herein by reference.

Over a period of time, medication deposits can accumulate within the internal flow passages of the pump mechanism 14. These medication deposits are believed to consist primarily of protein and other organic constituents produced particularly in narrow flow passage portions of the pump mechanism in the vicinity of the valve disk 44 and associated valve seat 46 of the inlet check valve 38. It is believed that these deposits occur as a result of shear denaturation and/or precipitation in response to substantial mechanical compression forces applied to complex pharmaceutical molecules as the valve disk 44 moves between open and closed positions.

Sufficient build-up of medication deposits can obstruct the inflow port to reduce pump performance characteristics. Moreover, accumulated deposits can eventually interfere with full closure of the check valve 38, and correspondingly result in undesirable back-flow leakage of body fluids from the patient into the medication chamber 12.

In accordance with the present invention, a relatively simple and effective yet clinically safe reconditioning process is provided for removing accumulated particle-like medication deposits from the internal flow passages of the pump mechanism 14, and especially at the check valve 38, to restore pump performance substantially to initial product specifications. The process of the present invention beneficially permits dissolution and removal of the medication deposits in an in situ manner, such that surgical removal of the implanted pump 10 for repair and/or replacement is not required.

In general terms, the reconditioning process of the present invention involves sequential delivery of liquid solutions to the implantable pump 10, by means of a hypodermic needle 26 to access the medication chamber 12 via the refill fitting 24. The cleaning solutions are introduced into the medication chamber 12 and thereafter delivered by operation of the pump mechanism 14 to the internal flow passages thereof. Residual cleaning solution may be aspirated from the medication chamber 12, at the conclusion of the cleaning process, by means of a hypodermic needle preparatory to refilling the chamber 12 with the selected medication.

As an initial step in accordance with the reconditioning process of the present invention, the medication chamber 12 is accessed via the refill fitting 24 to aspirate residual medication contained therein. In the case of back-flow leakage, the fluid aspirated from the medication chamber 12 will typically comprise a mixture of residual medication contaminated with body fluid.

The medication chamber 12 is then filled with a selected buffer solution 52, having a relatively neutral pH. While a variety of different buffer solutions may be used, a biocompatible phosphate buffer such as a solution of 0.2 Molar potassium phosphate having a pH of about 7.4 is preferred. If desired, the medication chamber may be filled with the buffer solution 52 and then aspirated to rinse residual fluids therefrom, prior to refilling of the medication chamber with the same buffer solution 52.

As shown in FIG. 4, the pump mechanism 14 is then operated in a normal manner to pump a sufficient quantity of the buffer solution 52 from the medication chamber 12 into the internal pump flow passages to substantially fill them. At the conclusion of this pumping step, buffer solution 52 remaining in the medication chamber 12 is aspirated via the refill fitting 24.

A selected rinse solution 54 is then injected through the refill fitting 24 into the medication chamber 12. The rinse solution 54 is selected to dissolve medication-based deposits within the pump mechanism 12, especially in the vicinity of the check valve 38. The rinse solution 54 may be either an alkaline solution or an acid solution. An alkaline solution must have a pH above approximately 10, and an acid solution must have a pH below approximately 4. Examples of acceptable alkaline solutions include potassium hydroxide, calcium hydroxide, amines such as triethylamine, and phosphines such as triethylphosphene. Examples of acceptable acid solutions include hydrochloric acid, sulfuric acid, nitric acid, acetic acid, and even Coca Cola.

In the preferred embodiment, the rinse solution 54 is an alkaline solution. Once again, although the specific rinse solution 54 may vary, a 0.01 Molar solution of sodium hydroxide having a pH of about 12 is preferred. The rinse solution 54 may be added to the medication chamber 12 and then aspirated to remove residual buffer solution, followed by refilling of the medication chamber with the rinse solution 54.

Figure 5:
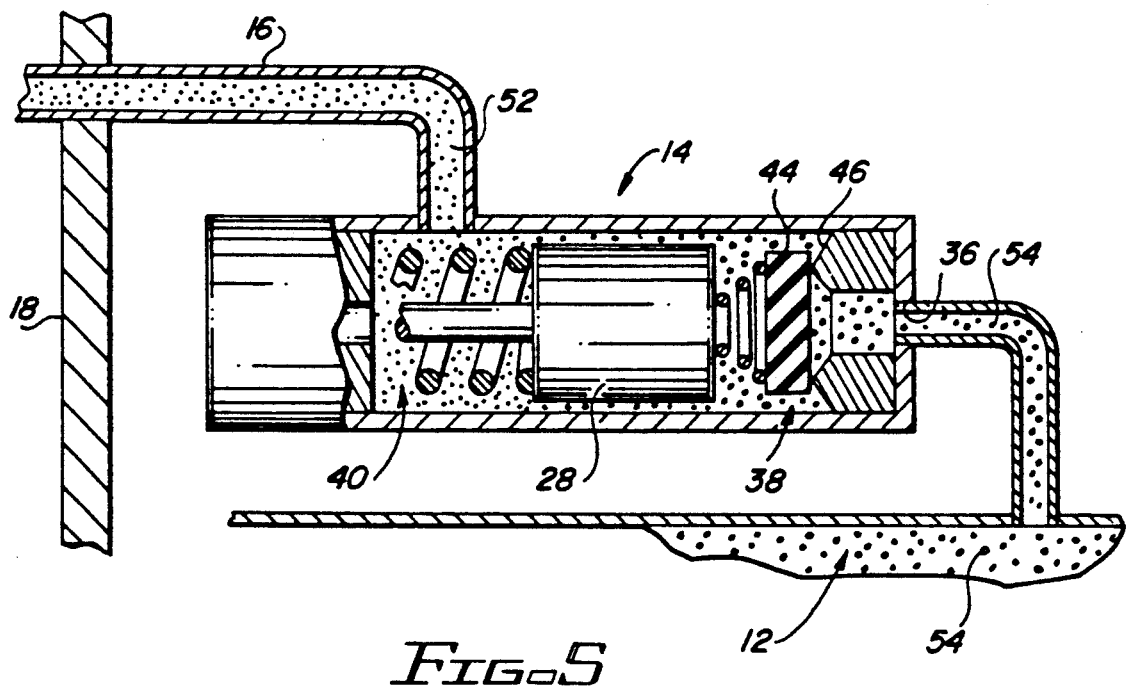
FIG. 5 is an enlarged fragmented sectional view corresponding with FIG. 4, showing the step of delivering a rinse solution to internal flow passages of the pump mechanism.

The pump mechanism 14 is then operated again, as viewed in FIG. 5, to deliver a selected volumetric dose of the rinse solution 54 into the internal pump flow passages. In the preferred sequence, the volume of rinse solution 54 drawn into the pump is selected to be somewhat less than the volume of internal pump flow passages. The rinse solution 54 is vigorous contacted with narrow pump passages, especially in the vicinity of the valve seat 46, since the valve disk 44 is displaced between the open and closed positions.

For example, in the MiniMed Technologies Model 2001 implantable insulin infusion pump, between approximately 40 and 100 microliters may be pumped, with the preferred volume being approximately 40 microliters. As a general guideline, a sufficient volume of the rinse solution 54 should be pumped to equal the volume of the pump and catheter, plus approximately 10 microliters. The rinse solution 54 will, however, be buffered in the catheter by the buffer solution 52, so only neutralized solution will reach the patient.

Such contact of the rinse solution 54 with medication deposits on the surfaces of the pump passages has been found to be effective in dissolving and removing the medication deposits for purposes of restoring normal pump characteristics and normal sealing operation of the inlet check valve 38. As the rinse solution 54 flows into the pump mechanism 14, past the check valve 38, the rinse solution contacts and intermixes with the buffer solution 52 in the outflow chamber 40, resulting in substantial neutralization of the rinse solution 54.

Residual rinse solution 54 within the medication chamber 12 is then aspirated through the refill fitting. An insulin diluent such as that commercially available from Hoechst, Aktiengesellschaft of Frankfurt, Germany, is then injected through the refill fitting 24 into the medication chamber 12, for purposes of preparing internal surfaces thereof to receive a charge of the selected medication. The medication chamber 12 may be rinsed with the insulin diluent in one or multiple steps, followed by aspiration of the diluent through the refill fitting. Finally, the medication chamber is recharged with the selected medication, such as Hoechst U400 insulin, injected into the medication chamber with a hypodermic needle engaged with the refill fitting 24.

The reconditioning process of the present invention has been demonstrated to be effective in removing medication deposits especially in the vicinity of the pump inlet check valve 38 to restore normal pump performance and normal sealing operation of the check valve 38. In addition, the process avoids exposure of the patient to the rinse solution 54, as a result of the intermixture of the rinse solution with the buffer solution for neutralization within the pump mechanism. The resultant effluent has been found to be nontoxic to the patient.

The process of the present invention has been described with reference to its use in an implantable infusion pump. However, its utility extends far beyond this application, and is useful in removing deposits on the diaphragm of a diaphragm infusion pump, deposits on the base of a piston in a piston infusion pump, and deposits in the tubing of a peristaltic infusion pump. It is also useful for removing deposits from other operating surfaces such as valves in infusion pumps.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. A method of reconditioning a medication infusion pump having a medication chamber for receiving and storing a supply of a selected medication, and a pump mechanism for delivering the medication in doses from the medication chamber to a patient, said reconditioning method comprising the steps of:
   placing a selected buffer solution into the medication chamber;
   operating the pump mechanism to draw a portion of the buffer solution from the medication chamber in an amount sufficient to substantially fill internal flow passages of the pump mechanism with the buffer solution;
   placing a selected rinse solution into the medication chamber; and
   operating the pump mechanism to draw a portion of the rinse solution from the medication chamber and into internal flow passages of the pump mechanism, whereby the rinse solution effectively contacts and cleans internal flow passage surfaces of the pump mechanism and then intermixes within the pump mechanism with the buffer solution for neutralization thereof.

2. A method as described in claim 1, wherein the selected rinse solution comprises:
   an alkaline rinse solution provided in a concentration sufficient to dissolve medication deposits within the pump mechanism.

3. A method as described in claim 2, wherein said alkaline rinse solution has a pH greater than approximately 10.

4. A method as described in claim 2, wherein said alkaline rinse solution comprises a solution from the group consisting of sodium hydroxide solution, calcium hydroxide solution, an amines solution, and a phosphines solution.

5. A method as defined in claim 2, wherein the selected rinse solution comprises:
   a sodium hydroxide solution.

6. A method as defined in claim 5, wherein the selected rinse solution comprises:
   an approximately 0.01 Molar sodium hydroxide solution.

7. A method as described in claim 1, wherein the selected rinse solution comprises:
   an acid rinse solution provided in a concentration sufficient to dissolve medication deposits within the pump mechanism.

8. A method as described in claim 7, wherein said acid rinse solution has a pH less than approximately 4.

9. A method as described in claim 7, wherein said acid rinse solution comprises a solution from the group consisting of hydrochloric acid, sulfuric acid, nitric acid, acetic acid, and Coca Cola.

10. A method as defined in claim 1, wherein the selected buffer solution comprises:
    a phosphate buffer solution.

11. A method as defined in claim 10, wherein said phosphate buffer solution comprises:
    an approximate 0.2 Molar potassium phosphate solution.

12. A method as defined in claim 1, wherein said step of operating the pump mechanism to draw a portion of the rinse solution from the medication chamber and into internal flow passages of the pump mechanism comprises:
    operating the pump mechanism to pump a volume of between approximately 40 and 100 microliters of the rinse solution.

13. A method as defined in claim 12, wherein said step of operating the pump mechanism to draw a portion of the rinse solution from the medication chamber and into internal flow passages of the pump mechanism comprises:
    operating the pump mechanism to pump a volume of between approximately 60 microliters of the rinse solution.

14. A method as defined in claim 1, wherein said step of operating the pump mechanism to draw a portion of the rinse solution from the medication chamber and into internal flow passages of the pump mechanism comprises:
    operating the pump mechanism to pump a volume approximately equal to the volume of the pump and catheter plus approximately 10 microliters of the rinse solution.

15. A method as defined in claim 1, further comprising the step of:
    aspirating residual medication from the medication chamber before placing the selected buffer solution therein.

16. A method as defined in claim 1, further comprising the step of:
    aspirating residual buffer solution from the medication chamber before placing the selected rinse solution therein.

17. A method as defined in claim 1, further comprising the steps of:
    aspirating residual rinse solution from the medication chamber after operating the pump mechanism to draw a portion of the rinse solution into flow passages of the pump mechanism; and
    refilling the medication chamber with the selected medication.

18. A method as defined in claim 1, wherein the infusion pump comprises a refill fitting for injecting fluids into and aspirating fluid from the medication chamber, said steps of placing the buffer and rinse solutions into the medication chamber comprising:
    injecting the solutions through the refill fitting.

19. A method as defined in claim 1, wherein said reconditioning method steps are performed in situ on a medication infusion pump implanted within the body of a patient.

20. In a medication infusion pump having a medication chamber for receiving and storing a selected medication, and a pump mechanism operable to draw the medication in doses from the medication chamber and to deliver the medication to a patient, a reconditioning method for cleaning medication deposits from internal flow passages of the pump mechanism, said method comprising the steps of:

placing a selected buffer solution into the medication chamber;

operating the pump mechanism to draw a sufficient quantity of the buffer solution from the medication chamber and into the pump mechanism to substantially fill the internal flow passages of the pump mechanism with the buffer solution;

removing residual buffer solution from the medication chamber;

placing a selected rinse solution into the medication chamber;

operating the pump mechanism to draw sufficient quantity of the rinse solution from the medication chamber to contact selected internal flow passage-defining surfaces of the pump mechanism to remove medication deposits from said selected internal surfaces, and in a quantity sufficiently less than the volumetric capacity of the pump mechanism internal flow passages whereby the rinse solution contacts and is substantially neutralized by buffer solution within the pump mechanism; and removing residual rinse solution form the medication chamber.

21. A method as defined in claim 20, wherein the infusion pump is an implantable pump having a transcutaneously accessible refill fitting, and further wherein said solution placing and removing steps are performed transcutaneously with a hypodermic needle for respectively injecting solution into and aspirating solution from the medication chamber.

22. The method and claim 20, further comprising the step of:

aspirating residual medication from the medication chamber before placing the selected buffer solution therein.

23. A method as defined in claim 20, further comprising the step of:

filling the medication chamber with medication subsequent to said step of removing residual rinse solution therefrom.

* * * * *